United States Patent
Kuhn et al.

(10) Patent No.: US 8,133,856 B2
(45) Date of Patent: Mar. 13, 2012

(54) CIS-3,3,5-TRIMETHYLCYCLOHEXYL ESTERS

(75) Inventors: Walter Kuhn, Holzminden (DE); Horst Surburg, Holzminden (DE)

(73) Assignee: Symrise AG, Holzminden (DE)

( * ) Notice: Subject to any disclaimer, the term of this patent is extended or adjusted under 35 U.S.C. 154(b) by 778 days.

(21) Appl. No.: 10/565,241

(22) PCT Filed: Jun. 30, 2004

(86) PCT No.: PCT/EP2004/051292
§ 371 (c)(1),
(2), (4) Date: Jan. 19, 2006

(87) PCT Pub. No.: WO2005/009492
PCT Pub. Date: Feb. 3, 2005

(65) Prior Publication Data
US 2006/0211597 A1    Sep. 21, 2006

(30) Foreign Application Priority Data
Jul. 19, 2003    (DE) .................................. 103 32 908

(51) Int. Cl.
*A61K 8/18*    (2006.01)
*A61K 8/00*    (2006.01)
*A61Q 13/00*    (2006.01)

(52) U.S. Cl. ............................................ 512/23; 512/1
(58) Field of Classification Search .................... 512/23, 512/1
See application file for complete search history.

(56) References Cited

U.S. PATENT DOCUMENTS

| | | | | |
|---|---|---|---|---|
| 4,136,066 A | * | 1/1979 | De Haan et al. | 512/24 |
| 5,306,707 A | * | 4/1994 | Burrell et al. | 512/2 |
| 5,856,590 A | * | 1/1999 | Emura et al. | 568/835 |
| 6,087,322 A | * | 7/2000 | Morelli et al. | 512/25 |
| 7,157,411 B2 | * | 1/2007 | Rohde et al. | 510/106 |
| 2003/0068295 A1 | * | 4/2003 | Rohde et al. | 424/76.1 |

FOREIGN PATENT DOCUMENTS

| | | | |
|---|---|---|---|
| DE | 20 26 409 A | | 12/1970 |
| DE | 24 06 849 A | | 9/1974 |
| DE | 23 26 061 A | | 12/1974 |
| DE | 25 18 392 | | 11/1976 |
| JP | 2002162112 | * | 6/2002 |
| WO | 01/43784 | * | 6/2001 |
| WO | WO 01/43784 | | 6/2001 |
| WO | WO 0143784 A2 | * | 6/2001 |

OTHER PUBLICATIONS

Formic Acid ILO icsc0485 {http://www.ilo.org/public/english/protection/safework/cis/products/icsc/dtasht/_icsc04/icsc0485.htm}.*
Grob et al. Helvetica Chimica Acta-vol. 47 No. 6 1964 pp. 1385-1401 with English Translation of p. 1399 .pdf.*
Caccamese et al., p. 546, col. 1, 1st paragraph, Chromatographia vol. 12 No. 8 pp. 545-547.*
Behura et al. (Current Science vol. 83 No. 11 pp. 1312-1313, 2002).*
1,8-cineole The Good Scents Company {http://www.thegoodscentscompany.com/data/rw1056361.html} product literature.*
Chowdhury et al. Bangladesh J. Sci. Ind. Res. 43 (2) pp. 259-266 2008.*
Eliel et al. Journal of Organic Chemistry 1970 vol. 35 No. 8 pp. 2716-2722.*
McClatchey (Economic Botany vol. 47 No. 3 pp. 291-291 1993 p. 291 introduction).*

* cited by examiner

*Primary Examiner* — Patrick Ryan
*Assistant Examiner* — Aaron Greso
(74) *Attorney, Agent, or Firm* — Roylance, Abrams, Berdo & Goodman, L.L.P.

(57) ABSTRACT

The present invention concerns mixtures with cis-3,3,5-trimethylcyclohexyl esters and trans-3,3,5-trimethylcyclohexyl esters, the use of cis-3,3,5-trimethylcyclohexyl esters as fragrance substances and individual cis-3,3,5-trimethylcyclohexyl esters and their uses.

18 Claims, No Drawings

CIS-3,3,5-TRIMETHYLCYCLOHEXYL ESTERS

FIELD OF THE INVENTION

The present invention concerns mixtures with cis-3,3,5-trimethylcyclohexyl esters and trans-3,3,5-trimethylcyclohexyl esters, the use of cis-3,3,5-trimethylcyclohexyl esters as fragrance substances and individual cis-3,3,5-trimethylcyclohexyl esters and their uses.

BACKGROUND OF THE INVENTION

In the perfume industry there is a fundamental need for new fragrance substances. With new fragrance substances the intention is to produce novel effects, to create new fashion trends and hence to satisfy the growing consumer demand for new, modern fragrance notes. Fragrances of this type should inherently be as original as possible and possess a high sensorial intensity and fullness. Even in low dosages they should allow sensorially perceptible, striking fragrance effects to be achieved.

Fragrance substances which are capable of imparting a near-natural scent to perfume compositions are particularly valuable here. Such near-naturalness can be achieved by the use of natural extracts such as flower extracts and essential oils, for example. However, because of the laborious manner in which they are obtained, natural products such as natural extracts are expensive, not available in unlimited quantities and subject to considerable fluctuations in quality. There is accordingly a need for synthesisable chemical substances and blends having a fragrance that is as near-natural as possible.

Mixtures of isomers of 3,3,5-trimethylcyclohexyl ester are known to be fragrance substances. For instance, S. Arctander, Perfume and Flavor Materials, Vol. I and II, Montclair, N.J., 1969, self-published, Monograph 3003, mentions 3,3,5-trimethylcyclohexyl acetate as exhibiting the following fragrance characteristics: weak, sweetly minty, herbal. A distinction is not made in this publication between the fragrance characteristics of cis- and trans-3,3,5-trimethylcyclohexyl acetate.

In Tluszcze, Srodki Piorace, Kosmetyki 19, 516-20 (1975) the olfactory characteristics of the formate, acetate and propionate of 3,3,5-trimethylcyclohexanol having a content of trans isomers of more than 95% are described. According to this publication, the formate smells of camphor, cineol, iris and sandalwood. The acetate apparently smells of woodland herbs with a thuja, lavender and spruce-like scent, this scent being described as being of interest and advantage to the perfume industry. The propionate supposedly has a mango-like aroma with a slight honey note and an iris-like background.

JP 01 056798 describes perfume oils for use in detergents containing bleach. 3,5,5-Trimethylcyclohexyl isobutyrate is listed as one of the possible perfume oils. Once again, no distinction is made between the cis and trans isomers.

WO 01/43784 describes the substances 3,3,5-trimethylcyclohexyl acetate, 3,3,5-trimethylcyclohexyl propionate, 3,3,5-trimethylcyclohexyl crotonate and 3,3,5-trimethylcyclohexyl butyrate and their use to neutralise unpleasant odours. The cited substances themselves apparently have only a very slight characteristic odour. In the olfactory assessment, no distinction is made here between the cis and trans isomers of these substances.

The object of the present invention was therefore to provide further fragrance substances which are as original as possible, have a high sensorial intensity and fullness and impart as near-natural a fragrance as possible to perfume compositions. In addition the fragrance substances should be obtainable with as consistent a quality as possible and by simple means.

The search for suitable fragrance substances, which led to the present invention, was made more difficult by the following facts:

The mechanisms of fragrance perception are not adequately known

The correlations between the special fragrance perception on the one hand and the chemical structure of the associated fragrance substance on the other have not been sufficiently researched There is no correlation between the fragrance characteristics and the toxicological safety of a substance Even minor changes to the structural make-up of a known fragrance substance frequently bring about major changes to the sensorial properties and reduce its compatibility for the human organism.

The success of the search for suitable fragrance substances is therefore highly dependent on the intuition of the person engaged in the search.

SUMMARY OF THE INVENTION

Surprisingly it has now been found that among the 3,3,5-trimethylcyclohexyl esters the cis-3,3,5-trimethylcyclohexyl esters are particularly valuable fragrance substances, whereas the trans-3,3,5-trimethylcyclohexyl esters are only of low olfactory value because they lack olfactory intensity and originality.

DETAILED DESCRIPTION OF THE INVENTION

The object is achieved according to the invention by a mixture comprising one or more cis-3,3,5-trimethylcyclohexyl esters and one or more trans-3,3,5-trimethylcyclohexyl esters, wherein the proportion of cis-3,3,5-trimethylcyclohexyl esters exceeds that of trans-3,3,5-trimethylcyclohexyl esters.

Although it is also stated in Tluszcze (see above) that mixtures having a content of trans-3,3,5-trimethylcyclohexyl ester also have interesting olfactory properties, this is probably attributable to the residual content of 5% cis-3,3,5-trimethylcyclohexyl ester. For example, trans-3,3,5-trimethylcyclohexyl acetate has only a comparatively slight olfactory intensity, with only a relatively weak ester-like and somewhat fruity odour and an associated rather unpleasant musty, camphoraceous, earthy note. In contrast, cis-3,3,5-trimethylcyclohexyl acetate has a bright, fresh-fruity, minty, herb-like, slightly floral-roselike scent. This considerable difference in the olfactory assessment was not foreseeable.

cis-3,3,5-Trimethylcyclohexyl ester(s) and mixtures containing this (these) ester(s), in particular those in which the proportion of cis-3,3,5-trimethylcyclohexyl ester exceeds the proportion of trans-3,3,5-trimethylcyclohexyl ester, are accordingly particularly suitable fragrance substances. They are characterised by a particular olfactory cleanliness and clarity, such that they can be used particularly effectively to create new, original and near-natural fragrance notes. The proportion of cis-3,3,5-trimethylcyclohexyl ester in a mixture should therefore preferably be over 80%, a proportion of over 85% and in particular a proportion of over 90% being particularly preferred for the specified reasons. Due to their quality and fullness, mixtures having a high proportion of the said cis isomers are markedly superior to corresponding mixtures of isomers having a low proportion of cis isomers in terms of the cleanliness and clarity of the fragrance perception.

Mixtures in which the proportion of cis-3,3,5-trimethylcyclohexyl ester is at least twice as high as that of trans-3,3,5-trimethylcyclohexyl ester are particularly preferred here. Due to this favourable ratio of isomers, such mixtures are particularly suitable for creating new, original and near-natural fragrance notes.

Mixtures are particularly preferred in which the cis- and trans-3,3,5-trimethylcyclohexyl esters are each mutually independently selected from the group consisting of 3,3,5-trimethylcyclohexyl formate, 3,3,5-trimethylcyclohexyl acetate, 3,3,5-trimethylcyclohexyl propionate, 3,3,5-trimethylcyclohexyl isobutyrate, 3,3,5-trimethylcyclohexyl butyrate, 3,3,5-trimethylcyclohexyl crotonate, 3,3,5-trimethylcyclohexyl tiglinate and 3,3,5-trimethylcyclohexyl-3-methyl-2-butenoate. The cited cis isomers each have particular characteristic fragrance notes, see below for more details. cis-3,3,5-Trimethylcyclohexyl esters and in particular the cited cis isomers are therefore particularly suitable for creating new, original and near-natural fragrance notes, either alone or in particular also mixed with the corresponding trans isomer.

To achieve the object it is also advantageous if the mixture comprises at least one further fragrance substance and thus forms a fragrance composition. Particularly interesting and natural, but also new and original fragrance notes can be created in this way. Fragrance substances which generally speaking are suitable for combining can be found for example in S. Arctander, Perfume and Flavor Materials, Vol. I and II, Montclair, N.J. 1969, self-published, or K. Bauer et al., Common Fragrance and Flavor Materials, 4th Edition, Wiley-VCH, Weinheim 2001. The following specific examples can be cited:

Extracts of natural raw materials such as essential oils, concretes, absolutes, resins, resinoids, balsams, tinctures, such as, for example ambergris tincture; amyris oil; angelica seed oil; angelica root oil; aniseed oil; valerian oil; basil oil; treemoss absolute; bay oil; mugwort oil; benzoin resin; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedarwood oil; cistus oil; citronella oil; citrus oil; copaiba balsam; copaiba balsam oil; coriander oil; costus root oil; cumin oil; cypress oil; davana oil; dill weed oil; dill seed oil; eau de brouts absolute; oakmoss absolute; elemi oil; tarragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; camomile blue oil; camomile Roman oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; litsea cubeba oil; bayleaf oil; mace oil; marjoram oil; mandarin oil; massoi bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange flower absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil; spike lavender oil; star anise oil; styrax oil; tagetes oil; fir needle oil; tea-tree oil; turpentine oil; thyme oil; tolu balsam; tonka absolute; tuberose absolute; vanilla extract; violet leaf absolute; verbena oil; vetiver oil; juniper berry oil; cognac oil; wormwood oil; wintergreen oil; ylang-ylang oil; hyssop oil; civet absolute; cinnamon leaf oil; cinnamon bark oil and fractions thereof, or ingredients isolated therefrom;

individual fragrance substances from the group comprising hydrocarbons, such as, for example, 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenyl methane;

aliphatic alcohols, such as, for example, hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methylene heptan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and acetals thereof, such as, for example, hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethyl acetal; 1,1-dimethoxy-2,2,5-trimethyl-4-hexene; citronellyl oxyacetaldehyde; 1-(1-methoxypropoxy)-(E/Z)-3-hexene;

aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

aliphatic sulfur-containing compounds, such as, for example, 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

aliphatic nitriles, such as, for example, 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

esters of aliphatic carboxylic acids, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octynoate; methyl-2-nonynoate; allyl-2-isoamyloxyacetate; methyl-3,7-dimethyl-2,6-octadienoate; 4-methyl-2-pentyl crotonate;

acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates and 3-methyl-2-butenoates thereof;

acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

cyclic terpene alcohols, such as, for example, menthol; isopulegol; alpha-terpineol; terpinenol-4; menthan-8-ol; menthan-7-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates and 3-methyl-2-butenoates thereof;

cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methyl cedryl ketone);

cyclic alcohols, such as, for example, 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols, such as, for example, alpha-3,3-trimethyl cyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers, such as, for example, cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyl-dodecahydronaphtho[2,1-b]furan; 1,5,9-trimethyl-13-oxabicyclo[10.1.0]trideca4,8-diene; rose oxide; 2-(2,4-dimethyl-3-cyclohexen-1-yl)-5-methyl-5-(1-methyl propyl)-1,3-dioxane;

cyclic and macrocyclic ketones, such as, for example, 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes, such as, for example, 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

cycloaliphatic ketones, such as, for example, 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl-(2,4-dimethyl-3-cyclohexen-1-yl) ketone;

esters of cyclic alcohols such as, for example, 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate, if the corresponding isomer is not already included in the mixture; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or -6-indenyl acetate; 4,7-methano-3a,4,5,6,7,7a-hexahydro-5 or -6-indenyl propionate; 4,7-methano-3a,4,5,6,7,7a-hexahydro-5 or -6-indenyl isobutyrate; 4,7-methanooctahydro-5 or -6-indenyl acetate;

esters of cycloaliphatic alcohols such as, for example, 1-cyclohexylethyl crotonate;

esters of cycloaliphatic carboxylic acids, such as, for example, allyl-3-cyclohexyl propionate; allyl cyclohexyloxyacetate; cis- and trans-methyl dihydrojasmonate; cis- and trans-methyl jasmonate; methyl-2-hexyl-3-oxocyclopentanecarboxylate; ethyl-2-ethyl-6,6-dimethyl-2-cyclohexenecarboxylate; ethyl-2,3,6,6-tetramethyl-2-cyclohexenecarboxylate; ethyl-2-methyl-1,3-dioxolane-2-acetate;

araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

araliphatic ethers, such as, for example, 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

aromatic and araliphatic ketones, such as, for example, acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzofuranyl ethanone; (3-methyl-2-benzofuranyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5', 6', 7', 8'-tetrahydro-3', 5', 5', 6', 8', 8'-hexamethyl-2-acetonaphthone;

aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethylbenzoate; ethyl-3-phenylglycidate; ethyl-3-methyl-3-phenylglycidate;

nitrogen-containing aromatic compounds, such as, for example, 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenoic acid nitrile; 3-methyl-5-phenyl pentanoic acid nitrile; methyl anthranilate; methyl-N-methyl anthranilate; Schiff bases of methyl anthranilate with 7-hydroxy-3,7-dimethyloctanal; 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropylpyrazine; 2-isobutyl-3-methoxypyrazine;

phenols, phenyl ethers and phenyl esters, such as, for example, estragole; anethole; eugenol; eugenyl methyl ether; isoeugenol; isoeugenyl methyl ether, thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

Combinations of the cis-3,3,5-trimethylcyclohexyl ester-containing mixture or these cis isomers with fragrance substances having a fresh and/or fruity note are particularly preferred. The cited cis isomers can enhance the fragrance impression of such fragrance substances particularly advantageously.

It is also preferable if the mixture or the fragrance composition contains cis-3,3,5-trimethylcyclohexyl ester in an adequate amount to shift the scent of the mixture towards a fresh and/or fruity note in comparison to a cis-3,3,5-trimethylcyclohexyl ester-free mixture having otherwise the same composition. The proportion of cis-3,3,5-trimethylcyclohexyl ester naturally depends in particular on the nature and concentration of the other constituents of the mixture. Often even a small proportion of cis-3,3,5-trimethylcyclohexyl ester causes the scent of the mixture to be given an olfactorily perceptible fresh and/or fruity fragrance note in comparison to a corresponding mixture without the cited cis isomer.

Such fragrance compositions wherein the proportion of cis-3,3,5-trimethylcyclohexyl ester is 0.1 to 90 wt. %, in particular 0.5 to 20 wt. %, particularly preferably 2 to 10 wt. %, relative to the total mass of the fragrance composition, are accordingly particularly preferred.

Due to their fragrance characteristics, cis-3,3,5-trimethylcyclohexyl esters are particularly suitable as fragrance substances. Particularly preferable according to the invention for use as fragrance substances are cis-3,3,5-trimethylcyclohexyl formate, cis-3,3,5-trimethylcyclohexyl acetate, cis-3,3,5-trimethylcyclohexyl propionate, cis-3,3,5-trimethylcyclohexyl isobutyrate, cis-3,3,5-trimethylcyclohexyl butyrate, cis-3,3,5-trimethylcyclohexyl crotonate, cis-3,3,5-trimethylcyclohexyl tiglinate and 3,3,5-trimethylcyclohexyl-3-methyl-2-butenoate.

cis-3,3,5-Trimethylcyclohexyl esters, mixtures or fragrance compositions of the type described above containing cis-3,3,5-trimethylcyclohexyl ester are particularly suitable for imparting, modifying and/or intensifying a fresh and/or fruity scent note.

In order to impart, modify and/or intensify a fresh and/or fruity scent in a perfume composition or in a perfumed product it is particularly suitable to add to the perfume composition or to the perfumed product a sensorially effective amount of a cis-3,3,5-trimethylcyclohexyl ester or a mixture or a fragrance composition of the type described above. In this way the aforementioned advantages can be realised with the cis-3,3,5-trimethylcyclohexyl esters or mixtures of the aforementioned type which contain them.

The use of cis-3,3,5-trimethylcyclohexyl formate is particularly preferred to impart, modify and/or intensify a scent having one, several or all of the following notes: fresh, terpene-like, natural, nutty and minty.

Also preferred is the use of cis-3,3,5-trimethylcyclohexyl acetate to impart, modify and/or intensify a scent having one, several or all of the following notes: brightly fresh-fruity, minty, herb-like and floral-roselike.

Additionally preferred is the use of cis-3,3,5-trimethylcyclohexyl propionate to impart, modify and/or intensify a scent having one, several or all of the following notes: fresh-fruity, terpene-like and apple-like.

cis-3,3,5-Trimethylcyclohexyl isobutyrate can be used particularly effectively to impart, modify and/or intensify a scent having one, several or all of the following notes: fruity, fresh-woody and pineapple-like.

cis-3,3,5-Trimethylcyclohexyl butyrate can be used particularly effectively to impart, modify and/or intensify a scent having one, several or all of the following notes: fruity and banana-like.

Likewise preferred is the use of cis-3,3,5-trimethylcyclohexyl tiglinate to impart, modify and/or intensify a scent having one, several or all of the following notes: fruity, plum-like, woody, damascenone-like.

The use of cis-3,3,5-trimethylcyclohexyl crotonate is also preferred to impart, modify and/or intensify a scent having one, several or all of the following notes: fresh, fruity, citrusy, plum-like, damascenone-like.

Also preferred is the use of cis-3,3,5-trimethylcyclohexyl-3-methyl-2-butenoate to impart, modify and/or intensify a scent having one, several or all of the following notes: woody, fresh, fruity, plum-like.

It goes without saying that two or more cis-3,3,5-trimethylcyclohexyl esters can also be mixed with one another and used as a fragrance substance, in particular to impart, modify and/or intensify a fresh and/or fruity note.

The invention also concerns compounds having the general formula

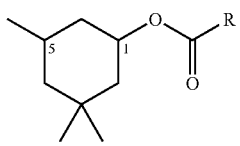

wherein C1 and C5 are each both R-configured or both S-configured (cis isomers) and wherein R is a branched or unbranched alkyl or alkenyl radical having 4 or more carbon atoms.

Such cis-3,3,5-trimethylcyclohexyl esters are particularly suitable for imparting, modifying and/or intensifying a fresh, fruity, plum-damascenone-like scent.

The cis-3,3,5-trimethylcyclohexyl esters according to formula (I) include in particular cis-3,3,5-trimethylcyclohexyl tiglinate, cis-3,3,5-trimethylcyclohexyl crotonate and cis-3,3,5-trimethylcyclohexyl-3-methyl-2-butenoate. The formula does not cover cis-3,3,5-trimethylcyclohexyl butyrate, which is nevertheless likewise particularly suitable for achieving the object because of its potential uses described above.

To synthesise 3,3,5-trimethylcyclohexyl esters having a high content of cis isomers the person skilled in the art will advantageously start from 3,3,5-trimethylcyclohexanol having a correspondingly high content of the cis isomer. This is readily accessible by hydrogenation of isophorone (3,3,5-trimethyl-2-cyclohexen-1-one), as described for example in the laid-open specification DE 10160009 A1.

The 3,3,5-trimethylcyclohexyl esters are produced in a manner known per se by reacting the 3,3,5-trimethylcyclohexanol with a corresponding carboxylic acid or a corresponding carboxylic anhydride or halide.

Perfume oils containing cis-3,3,5-trimethylcyclohexyl esters—in particular the substances, mixtures and fragrance compositions according to the invention described above—can be used for perfuming applications in liquid form, undiluted or diluted with a solvent. Suitable solvents for this purpose are, for example, ethanol, isopropanol, diethylene glycol monoethyl ether, glycerol, propylene glycol, 1,2-butylene glycol, dipropylene glycol, diethyl phthalate, triethyl citrate, isopropyl myristate, etc.

The perfume oils containing the two 3,3,5-trimethylcyclohexyl esters according to the invention or the mixtures or fragrance compositions described above can also be adsorbed on a support, which ensures both a fine distribution of the fragrance substances in the product and a controlled release during use. Such supports can be porous inorganic materials such as light sulfate, silica gels, zeolites, gypsums, clays, clay granules, gas concrete, etc., or organic materials such as woods, cellulose-based substances, sugars or plastics such as PVC, polyvinyl acetates or polyurethanes.

Perfume oils containing the two 3,3,5-trimethylcyclohexyl esters according to the invention or the mixtures or fragrance compositions described above can also be used in microencapsulated or spray-dried form, in the form of inclusion complexes or extrusion products and added in this form to the product to be perfumed.

The properties of the perfume oils modified in such a way can optionally be further optimised by coating with suitable materials with a view to a more selective fragrance release, waxy plastics such as e.g. polyvinyl alcohol being preferably used.

Microencapsulation of the perfume oils can take place by means of the so-called coacervation process, for example, using capsule materials made from polyurethane-like substances or soft gelatine, for example. The spray-dried perfume oils can be prepared by spray drying an emulsion or dispersion containing the perfume oil, for example, wherein modified starches, proteins, dextrin and vegetable gums can be used as supports. Inclusion complexes can be prepared by, for example, introducing dispersions of the perfume oil and cyclodextrins or urea derivatives into a suitable solvent, e.g. water. Extrusion products can be obtained by melting the perfume oils with a suitable waxy substance and by extrusion with subsequent solidification, optionally in a suitable solvent, e.g. isopropanol.

Perfume oils containing the two 3,3,5-trimethylcyclohexyl esters according to the invention or the mixtures or fragrance compositions described above can be used in concentrated form, in solutions or in the aforementioned modified form for the production of e.g. perfume extracts, eau de parfums, eau de toilettes, aftershaves, eau de colognes, preshave products, splash colognes and perfumed refreshing wipes, and for the perfuming of acid, alkaline and neutral cleaning agents, such as e.g. floor cleaners, window cleaners, washing-up liquids, bath and sanitary cleaners, scouring agent, solid and liquid WC cleaners, powdered and foaming carpet cleaners, textile fresheners, ironing aids, liquid detergents, powdered detergents, laundry pretreatment agents such as bleaches, soaking agents and stain removers, fabric softeners, laundry soaps, detergent tablets, disinfectants, surface disinfectants and air fresheners in liquid or gel form or applied to a solid support, aerosol sprays, waxes and polishes such as furniture polishes, floor waxes, shoe creams and personal care products such as e.g. solid and liquid soaps, shower gels, shampoos, shaving soaps, shaving foams, bath oils, cosmetic emulsions of the oil-in-water, water-in-oil and water-in-oil-in-water type, such as e.g. skin creams and lotions, face creams and lotions, sun creams and lotions, aftersun creams and lotions, hand creams and lotions, foot creams and lotions, depilatory creams and lotions, aftershave creams and lotions, tanning creams and lotions, haircare products such as e.g. hair sprays, hair gels, hair setting lotions, hair rinses, permanent and semi-permanent hair colorants, hair sculpting agents such as cold waves and hair smoothing agents, hair waters, hair creams and lotions, deodorants and antiperspirants such as e.g. underarm sprays, roll-ons, deodorant sticks, deodorant creams, decorative cosmetic products such as e.g. eyeshadows, nail polishes, foundations, lipsticks, mascara, and of candles, lamp oils, incense sticks, insecticides, repellents and fuels.

The invention is illustrated in greater detail below by reference to examples, without being restricted to these examples:

EXAMPLES

Example 1

Preparation of 3,3,5-Trimethylcyclohexyl Acetate Having A High Content of Cis Isomers 568 g of 3,3,5-trimethylcyclohexanol having a cis content of 90%, produced in accordance with DE 10160009 A1, are placed in a 2-l three-necked flask with a top-mounted distillation device (20-cm packed column with still head and packed with glass rings) and dropping funnel. After application of a weak vacuum (approx. 600 mbar), the contents are heated to a bottoms temperature of approx. 140° C. and 612 g of acetic anhydride are slowly metered in. Acetic acid that is formed is distilled off. At the end of the metered addition, the batch is held at the same temperature for a further one hour. Fractional distillation is then performed. The 3,3,5-trimethylcyclohexyl acetate obtained boils at an overhead temperature of approx. 85° C. under 1 mbar vacuum. The yield is 700 g, corresponding to 95% of theoretical; the cis content of the 3,3,5-trimethylcyclohexyl acetate obtained in this way is 90%.

The corresponding cis-3,3,5-trimethylcyclohexyl ester of formic acid is prepared in an analogous manner, using the mixed anhydride of acetic anhydride and formic acid.

Example 2

Preparation of Further Esters of 3,3,5-Trimethylcyclohexyl Acetate Having A High Content of Cis Isomers

Example 2a cis-3,3,5-Trimethylcyclohexyl crotonate 71 g of 3,3,5-trimethylcyclohexanol having a cis content of 90% are placed in a 1-l reaction flask together with 60 g of pyridine in 300 ml of methyl tert-butyl ether and 63 g of crotonic acid chloride are added at 0 to 5° C. over 30 minutes. The reaction mixture is left to continue reacting for a further one hour at this temperature; it is then allowed to heat up to room temperature. After one hour it is heated for a further 30 min to 50° C. After cooling, it is fractionated with water, the organic phase is separated off and first washed with dilute hydrochloric acid and then stirred for a further 30 min with 5-percent sodium hydroxide solution. After washing until it is neutral, the solvent is drawn off and the residue distilled using a short column. 63 g of pure 3,3,5-trimethylcyclohexyl crotonate having a cis content of 90% are obtained at a boiling point of 121° C. under 20 mbar. MS: 210 (M*, 0,3), 195 (0,5), 141 (3), 124 (75), 109 (100), 95 (24), 87 (24), 82 (25), 69 (75), 55 (11), 41 (33). The cis-3,3,5-trimethylcyclohexyl esters of propionic acid, isobutyric acid and butyric acid can be prepared in an analogous manner.

Example 2b cis-3,3,5-Trimethylcyclohexyl tiglinate 71 g of 3,3,5-trimethylcyclohexanol having a cis content of 90%, 60 g of tiglic acid and 1 g of p-toluene sulfonic acid are boiled in a water separator until there was no further noticeable water separation. The reaction solution is deacidified with dilute sodium hydroxide solution and washed with water until neutral. After drawing off the solvent the residue is distilled using a short column. 65 g of pure 3,3,5-trimethylcyclohexyl tiglinate having a cis content of 90% are obtained at a boiling point of 127-130° C. under 19 mbar. MS: 224 (M+, 0,5), 209 (0,4), 141 (3), 124 (72), 109 (100), 101 (60), 95 (22), 83 (68), 69 (31), 55 (42), 41 (17).

Example 2c cis-3,3,5-Trimethylcyclohexyl-3-methyl-2-butenoate 85.2 g of 3,3,5-trimethylcyclohexanol, 68.4 g of methyl-3-methyl-2-butenoate and 3 g of sodium methylate are heated until no more methanol, which is removed via a short top-mounted distillation column, is eliminated. After cooling, the reaction mixture is fractionated with water and methyl tert-butyl ether is added. The organic phase is washed with dilute sulfuric acid, dilute sodium hydroxide solution and water and concentrated to low volume. The residue is fractionated using a short distillation column. 109 g of pure 3,3,5-trimethylcyclohexyl-3-methyl-2-butenoate having a cis content of 90% are obtained at a boiling point of 131° C. under 20 mbar. MS: 224 (M*, 0,3), 209 (0,2), 141 (6), 124 (32), 109 (49), 101 (60), 95 (12), 83 (100), 69 (36), 55 (28), 41 (15).

Example 3

Preparation of a Fragrance Composition According to the Invention

A perfume base is prepared by mixing the following synthetic fragrance substances (all figures in parts by weight):

| | |
|---|---|
| Benzyl acetate | 30 |
| Ozonil* (2-tridecene nitrile) 10% in diethyl phthalate | 5 |
| Dihydromyrcenol | 150 |
| Decanal | 1 |
| 2-Phenoxyethyl isobutyrate | 100 |
| Methyl cedryl ketone | 35 |
| Hexyl cinnamaldehyde | 50 |
| Lilial ® | 30 |
| Linalyl acetate | 100 |
| Galaxolide ® 50% in diethyl phthalate | 10 |
| Cedryl acetate | 30 |
| Zibeth absolute synth. | 1 |
| Citrus terpene | 70 |
| Ethyl vanillin | 3 |
| gamma-Undecalactone | 1 |
| Citronitril* (3-methyl-5-phenyl-2-pentene nitrile) | 10 |
| Projasmon P* (2-heptylcycloheptanone) | 1 |
| Agrumex HC* (2-tert-butyl cyclohexyl acetate) | 30 |
| Hexenyl isobutyrate, cis/trans | 1 |
| Hexenyl acetate, cis/trans | 1 |
| Limette oil synth. | 10 |
| Diethyl phthalate | 266 |
| Total | 935 |

*Tradenames of Symrise GmbH & Co KG, Holzminden, Germany

This fragrance composition is given an extremely natural green-fresh, herb-like and fruity character by the addition of 65 parts by weight of 3,3,5-trimethylcyclohexyl acetate with a content of cis isomers of 90%. The vibrancy and attractiveness are markedly and perceptibly increased.

The addition of 3,3,5-trimethylcyclohexyl acetate with a content of cis isomers of 90% gives the mixture a natural vibrancy and supports the fresh and fruity head note.

The invention claimed is:
1. Mixture comprising one or more cis-3,3,5-trimethylcyclohexyl esters and one or more trans-3,3,5-trimethylcyclohexyl esters, wherein the proportion of cis-3,3,5-trimethylcyclohexyl esters exceeds that of trans-3,3,5-trimethylcyclohexyl esters, wherein the cis- and trans-3,3,5-trimethylcyclohexyl esters are each mutually independently selected from the group consisting of 3,3,5-trimethylcyclohexyl acetate, 3,3,5-trimethylcyclohexyl propionate, 3,3,5-trimethylcyclohexyl isobutyrate, 3,3,5-trimethylcyclohexyl butyrate, 3,3,5-trimethylcyclohexyl crotonate, 3,3,5-trimethylcyclohexyl tiglinate and 3,3,5-trimethylcyclohexyl-3-methyl-2-butenoate, where the mixture comprises at least 80 wt % cis-3,3,5-trimethylcyclohexyl esters and said trans-3,3,5- trimethylcyclohexyl ester being present in an amount of more than 0 wt % and 0 no more than 20 wt %, based on a total mass of the mixture.

2. Mixture according to claim 1, characterised in that the proportion of cis-3,3,5-trimethylcyclohexyl ester is at least twice as high as that of trans-3,3,5-trimethylcyclohexyl ester.

3. Mixture according to claim 1, containing one or more cis-3,3,5-trimethylcyclohexyl esters in an adequate amount to make the scent of the mixture fresher and/or fruitier in comparison to a cis-3,3,5-trimethylcyclohexyl ester-free mixture having otherwise the same composition.

4. Fragrance composition comprising a mixture according to claim 1 and at least one further fragrance substance.

5. A method for enhancing a fragrance note of a fragrance composition by adding thereto a cis-3,3,5-trimethylcyclohexyl ester selected from 3,3,5-trimethylcyclohexyl propionate, 3,3,5-trimethylcyclohexyl isobutyrate, 3,3,5-trimethylcyclohexyl butyrate, 3,3,5-trimethylcyclohexyl crotonate, 3,3,5-trimethylcyclohexyl tiglinate and 3,3,5-trimethylcyclohexyl-3-methyl-2-butenoate, wherein the composition comprises 0.1 to 90 wt % of said cis-3,3,5-trimethylcyclohexyl ester, relative to the total mass of the fragrance composition.

6. The method for enhancing a composition by adding thereto a cis-3,3,5-trimethylcyclohexyl ester according to claim 5 to impart, modify and/or intensify a fresh and/or fruity scent note.

7. Process for imparting, modifying and/or intensifying a fresh and/or fruity scent in a perfume composition or in a perfumed product, characterised in that a sensorially effective amount of a cis-3,3,5-trimethylcyclohexyl ester according to claim 1 is added to the perfume composition or to the product.

8. A method for enhancing a fragrance note of a fragrance composition by adding thereto a cis-3,3,5-trimethylcyclohexyl ester to impart, modify and/or intensify a scent having one or more of the following notes: fresh, terpene-like, natural, nutty and minty, wherein the composition includes at least 80 wt % cis-3,3,5-trimethylcyclohexyl ester, relative to the total mass of the composition.

9. A method for enhancing a fragrance note of a fragrance composition by adding thereto cis-3,3,5-trimethylcyclohexyl propionate to impart, modify and/or intensify a scent having one, several or all of the following notes: fresh-fruity, terpene-like and apple-like, wherein the composition includes 0.1 to 90 wt % cis-3,3,5-trimethylcyclohexyl ester, relative to the total mass of the fragrance composition.

10. A method for enhancing a fragrance note of a fragrance composition by adding thereto cis-3,3,5-trimethylcyclohexyl isobutyrate to impart, modify and/or intensify a scent having one, several or all of the following notes: fruity, fresh-woody and pineapple-like, wherein the composition includes 0.1 to 90 wt % cis-3,3,5-trimethylcyclohexyl ester, relative to the total mass of the fragrance composition.

11. A method for enhancing a fragrance note of a fragrance composition by adding thereto cis-3,3,5-trimethylcyclohexyl butyrate to impart, modify and/or intensify a scent having one, several or all of the following notes: fruity and banana-like, wherein the composition includes 0.1 to 90 wt % cis-3,3,5-trimethylcyclohexyl ester, relative to the total mass of the fragrance composition.

12. A method for enhancing a fragrance note of a fragrance composition by adding thereto cis-3,3,5-trimethylcyclohexyl tiglinate to impart, modify and/or intensify a scent having one, several or all of the following notes: fruity, plum-like, woody, damascenone-like, wherein the composition includes 0.1 to 90 wt % cis-3,3,5-trimethylcyclohexyl ester, relative to the total mass of the fragrance composition.

13. A method for enhancing a fragrance note of a fragrance composition by adding thereto cis-3,3,5-trimethylcyclohexyl crotonate to impart, modify and/or intensify a scent having one, several or all of the following notes: fresh, fruity, citrusy, plum-like, damascenone-like, wherein the composition includes 0.1 to 90 wt % cis-3,3,5-trimethylcyclohexyl ester, relative to the total mass of the fragrance composition.

14. A method for enhancing a fragrance note of a fragrance composition by adding thereto cis-3,3,5-trimethylcyclohexyl-3-methyl-2-butenoate to impart, modify and/or intensify a scent having one, several or all of the following notes: woody, fresh, fruity, plum-like, wherein the composition includes 0.1 to 90 wt % cis-3,3,5-trimethylcyclohexyl ester, relative to the total mass of the fragrance composition.

15. The method of claim 5, wherein said composition further comprises a further fragrance substance and where said cis-3,3,5-trimethylcyclohexyl ester is included in an amount of at least 80 wt % based on the total weight of the fragrance component and cis-3,3,5-trimethylcyclohexyl ester.

16. The method of claim 15, wherein said fragrance component is a trans-3,3,5-trimethylcyclohexyl ester.

17. The method of claim 5, wherein said cis-3,3,5-trimethylcyclohexyl ester is added in an amount of 0.5 to 20 wt % based on the total weight of the composition.

18. The method of claim 5, wherein said cis-3,3,5-trimethylcyclohexyl ester is added in an amount of 2 to 10 wt % based on the total weight of the composition.

* * * * *

UNITED STATES PATENT AND TRADEMARK OFFICE
CERTIFICATE OF CORRECTION

PATENT NO. : 8,133,856 B2
APPLICATION NO. : 10/565241
DATED : March 13, 2012
INVENTOR(S) : Kuhn et al.

It is certified that error appears in the above-identified patent and that said Letters Patent is hereby corrected as shown below:

(Column 13, line 2), delete the second occurrence of "0".

Signed and Sealed this
Twenty-ninth Day of May, 2012

David J. Kappos
*Director of the United States Patent and Trademark Office*